United States Patent [19]

Lindstrom et al.

[11] Patent Number: 4,495,200

[45] Date of Patent: Jan. 22, 1985

[54] PROCESS FOR THE CONTROL OF SULFATE-REDUCING BACTERIA

[75] Inventors: Merlin R. Lindstrom, Bartlesville; Leslie J. Henshaw, Stillwater; Harold W. Mark; James B. Clark, both of Bartlesville, all of Okla.

[73] Assignee: Phillips Petroleum Company, Bartlesville, Okla.

[21] Appl. No.: 539,441

[22] Filed: Oct. 6, 1983

[51] Int. Cl.$^3$ .............................................. A01N 47/10
[52] U.S. Cl. ................... 424/286; 252/8.55 E; 252/391; 252/402; 422/16; 210/764
[58] Field of Search .................. 252/8.55 E, 8.55 R, 252/391, 402; 424/286; 210/764; 71/67, 90, 111; 422/16

[56] References Cited

U.S. PATENT DOCUMENTS

| | | | |
|---|---|---|---|
| 2,921,953 | 1/1960 | Kruse et al. | 260/455 |
| 2,987,475 | 6/1961 | Legator | 252/8.55 |
| 3,085,043 | 4/1963 | Beaver et al. | 424/286 |
| 3,198,733 | 8/1965 | Pera et al. | 252/8.55 |
| 3,377,346 | 4/1966 | Leber et al. | 260/246 |
| 3,674,457 | 7/1972 | Wolfson | 71/67 |
| 3,699,231 | 10/1972 | Werlein et al. | 424/286 |
| 4,285,765 | 8/1981 | Pera et al. | 162/161 |
| 4,293,559 | 10/1981 | Buckman et al. | 424/270 |

OTHER PUBLICATIONS

Layman, "New biocides find acceptance difficult", *C & EN*, Apr. 12, 1982, pp. 10–11, and following (2 pp.).
Ruseska et al., "Biocide testing against corrosion-causing oil-field bacteria helps control plugging", Technology, Mar. 8, 1982, *Oil & Gas Journal*, pp. 253, 254, 256, 261, 262, and 264.

*Primary Examiner*—Josephine L. Barr

[57] ABSTRACT

A process for the control of planktonic sulfate-reducing bacteria in industrial process water systems which comprises the step of treating said system with a dithiocarbamate of the formula:

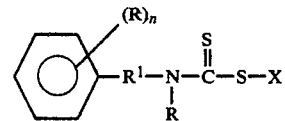

wherein R is a $C_1$ to $C_4$ alkyl radical, $R^1$ is either a methylene or ethylene radical, n is 0, 1, 2, or 3 and X is a Group IA alkali metal.

4 Claims, No Drawings

PROCESS FOR THE CONTROL OF SULFATE-REDUCING BACTERIA

This invention relates to a process for the control of sulfate-reducing bacteria; exemplified by bacteria of the genus Desulfovibrio.

Sulfate-reducing bacteria are generally present in waters used for the secondary recovery of petroleum. The presence of these bacteria is objectionable if not controlled. For example, these organisms are able to reduce sulfates present in the injection water to sulfides which in turn react with soluble iron salts to form insoluble iron sulfide. As a result, matted deposits are produced consisting of sulfides, occluded oil, plus any other solids that may be present. This is undesirable because water containing such deposits when injected into subterranean formations causes the plugging thereof. Furthermore, sulfate-reducing bacteria cause corrosion of metal by accelerating galvanic action. Microbiological corrosion is well recognized and is a major economic problem in the petroleum industry.

The microorganisms present in water which may be classified broadly as sulfate-reducing bacteria include many species of spore-forming and non-spore-forming bacteria, but in general sulfate reducing microorganisms belonging to the genus Desulfovibrio cause the most difficulty. Although several species of Desulfovibrio are found, such as *D. desulfuricans, D. aestuarii,* and *D. salexigens; D. desulfuricans* is the most common species isolated, both in frequency and objectionable properties. It is to be understood that although the term "sulfate-reducing bacteria" conveys only a physiological and not a taxonomic meaning, it is used herein to include all bacteria and bacteria-like organisms which are characterized by their ability to reduce sulfates to sulfides. Such organisms will be recognized by qualified bacteriologists as belonging to several taxonomic genera but most often as belonging to the well known and characterized genus Desulfovibrio. For that reason this invention is applicable directly to all sulfate-reducing bacteria.

Heretofore, it has been particularly difficult to control the growth of planktonic sulfate-reducing bacteria by means of anti-microbial agents. Organomercurial compounds are generally the most effective and versatile anti-microbial compounds known. In many cases, these compounds will inhibit the growth of bacteria other than sulfate-reducing bacteria at a concentration of less than 1 ppm. However, much higher concentrations are required to inhibit sulfate-reducing bacteria.

Although chlorine and hypochlorite are effective anti-microbial agents, the use of these compounds to control planktonic sulfate-reducing bacteria in he petroleum industry is limited. This is true because the available chlorine tends to react with suspended materials present in these waters. Thus unless a rather large quantity of chlorine or the hypochlorite is used, no available chlorine will be present to act as a bacteriocide. If a sufficient quantity of either is used to provide an excess over that required for reacting with the suspended materials, the excess of chlorine or hypochlorite used will itself cause corrosion.

U.S. Pat. No. 3,198,733 discloses the use of dialkyldithiocarbamate salts as bacteriostatic agents against sulfate-reducing bacteria. Bacteriostatic agents function to inhibit microbial cell growth without directly killing the microbial cells. If the normally bacteriostatic agents are capable of any bacteriocidal activity at all they must typically be employed at prohibitively high concentration levels such as in sea water. Therefore, a process for not only inhibiting the growth of sulfate-reducing bacteria but also for imparting biocidal activity against them particularly in sea water is highly desirable.

Therefore, an object of this invention is to provide an improved process, for the control of planktonic sulfate-reducing bacteria, which imparts bacteriocidal activity as well as bacteriostatic activity.

Other aspects, objects, and advantages of the present invention will be apparent from the specification and the appended claims.

In accordance with the present invention it has been discovered that bacteriocidal activity as well as bacteriostatic activity is imparted against planktonic sulfate-reducing bacteria by treating waters containing the sulfate bacteria with an alkali metal salt of a dithiocarbamate compound of the formula:

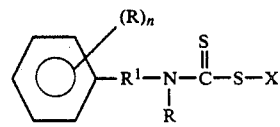

wherein R is a $C_1$ to $C_4$ alkyl radical, $R^1$ is either a methylene or ethylene radical, n is 0, 1, 2, or 3 and X is a Group IA alkali metal.

In the above formula, $R^1$ is preferably a methylene radical and X is preferably lithium, sodium, or potassium, most preferably sodium. Thus, Na-N-benzyl, N-methyl-dithiocarbamate is the preferred dithiocarbamate for use in the process of the present invention.

The dithiocarbamate compounds of the present invention are conveniently prepared by the recognized method which comprises adding carbon disulfide to a mixture of the appropriate amine and alkali metal hydroxide, each in an equimolar proportion, in an aqueous medium, according to the following equation:

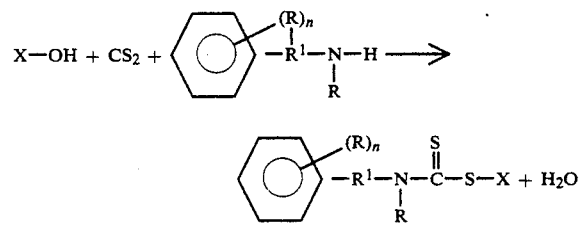

wherein R, $R^1$, n, and X are as previously herein defined.

It is not necessary to isolate the resulting compound, which is obtained in substantially stoichiometric yield, since the solution may be used as such.

The process of the present invention is effective against planktonic as opposed to sessile sulfate-reducing bacteria. Planktonic bacteria are broadly defined as floating bacteria whereas sessile bacteria are colonized.

The quantity of dithiocarbamate employed in the process of the present invention may vary within very wide limits but in general should not be less than 1 ppm, nor, for practical purposes exceed 10,000 ppm. An optimum quantity for most cases is between 10 ppm and 500 ppm. The effective amount or concentration of the dithiocarbamate to be used will vary according to the specific system in which the compositions are used. For example, the Examples will show that, quite surprisingly, relatively higher concentrations of Na-N-benzyl-N-methyl-dithiocarbamate must be used to impart biocidal activity against sulfate-reducing bacteria present in fresh water systems (i.e., less than 300 ppm total dissolved solids) than in salt water systems (i.e., 300 ppm total dissolved solids or greater).

It will be understood, however, that the quantity or concentration of the dithiocarbamate employed and the effective control obtained by it may vary greatly without departing from the scope of the invention. Generally speaking, it is preferable to employ the dithiocarbamate in the present invention in an effective amount or concentration such that the bacteria will be killed (or their growth properly controlled) in the shortest possible time.

The following Examples illustrate the present invention.

EXAMPLE I

Measurement of Bacteriostatic Activity

Various chemicals to be tested for bacteriostatic activity were each dissolved in 0.9 ml of distilled water in concentrations to give the final concentration desired in a total volume of 10 ml. Each chemical in the desired concentration was added to 9 ml standard medium in an API 38 SRB bottle. Each bottle was then inoculated with 0.1 ml of a stationary phase of *Desulfovibrio desulfuricans* (NRRL B-4304). Thus the total volume of diluted chemical agent to be tested (0.9 ml), API 38 SRB bottle medium (9 ml) and inoculated *Desulfovibrio desulfuricans* culture (0.1 ml) was 10 ml.

The inoculated bottles were then incubated at 28° C. and observed daily for 28 days. Survival of the cells was indicated by the formation of FeS as a black precipitate in the vials.

The results of the bacteriostatic test for various chemical substances are given in Table I. The minimal concentration of chemical which was found to be inhibitory (bacteriostatic) is given as a concentration in ppm.

TABLE I

| Chemical Tested | Bacteriostatic Concentration Range (ppm) in Distilled Water |
|---|---|
| NaN—benzyl-N—methyl-dithiocarbamate (A) | 10 |
| K—N—methyl-N—hydroxymethyl dithiocarbamate (B) | >500 |
| Zn—di-n-butyl-dithiocarbamate (C) | >500 |
| Na—di-n-butyl-dithiocarbamate (D) | 100 |
| Na—dimethyl-dithiocarbamate (E) | >500 |
| 15% Na—dimethyl-dithiocarbamate + 15% disodium ethylene-bis-dithiocarbamate (F) | 500 |

The above data show that quite surprisingly bacteriostatic agent (A) is much more effective against *D. desulfuricans* than either (B), (C), (D), (E), and (F). In some instances, (A) was effective at least 1/50 the concentration level of other agents [(B), (C), (E), and (F)]. (A) was ten times more effective as a bacteriostatic agent than (B).

EXAMPLE II

Measurement of Bacteriocidal Activity

Nine ml quantities of a synthetic oil field water (Arkansas-Burbank water which is essentially fresh water containing less than about 500 ppm total dissolved solids) were added to serum vials. Oxygen was removed by degassing and sealing in an anaerobic hood. These anaerobic vials were then autoclaved.

One ml concentrations of each chemical to be tested for biocidal activity were aseptically added to each vial by hypodermic syringe to give final concentrations in 10 ml required for the testing range. Concentrations were calculated in ppm of active ingredient.

Each of the vials was then inoculated with 0.1 ml of a stationary phase culture of *Desulfovibrio desulfuricans* (NRRL B-4304).

After 24 hours contact time, 0.1 ml of the contents of each vial were transferred by hypodermic syringe to a standard API 38 SRB bottle. These were incubated at 28° C. and observed daily for 28 days. Survival of the cells was indicated by the formation of FeS as a black precipitate in the vials.

The above tests were repeated using a synthetic sea water in place of the synthetic oil field water.

The results of each test are given in Table II. The minimal concentration of chemical which was found to be bacteriocidal is given as a concentration in ppm.

TABLE II

| Chemical Tested | Bacteriocidal Concentration Range (ppm) | |
|---|---|---|
| | Arkansas-Burbank Water | Sea Water |
| Chemical Tested (A) | 500 | 80 |
| Chemical Tested (B) | >500 | >500 |
| Chemical Tested (C) | >500 | 500 |
| Chemical Tested (D) | >500 | 500 |
| Chemical Tested (E) | >500 | >500 |
| Chemical Tested (F) | >500 | >500 |

The above data indicate that, in Arkansas-Burbank water, (A) was found to be biocidal at a concentration of 500 ppm while the others, (B) through (F), were found not to be biocidal at 500 ppm and therefore are presumably biocidal only at high concentrations, i.e. above 500 ppm.

In sea water, (A) was found quite surprisingly to be biocidal at a concentration of 80 ppm which is considerably below the 500 ppm or higher level found for the others, i.e. (B) through (F). This result is quite significant considering the fact that one skilled in the art generally recognizes bacteriocides as being ineffective at low concentrations, i.e. 100 ppm, in sea water.

Reasonable variations and modifications are possible from the foregoing without departing from either the spirit or scope of the present invention.

We claim:

1. A process for the control of planktonic sulfate-reducing bacteria in industrial process water systems which comprises the step of treating said systems with a dithiocarbamate of the formula:

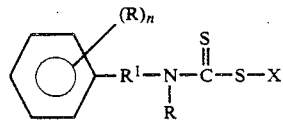

wherein R is a $C_1$ to $C_4$ alkyl radical, $R^1$ is either a methylene or ethylene radical, n is 0, 1, 2, or 3 and X is a Group IA alkali metal and wherein said dithiocarbamate is incorporated into the said water systems in a concentration between about 1 ppm and 10,000 ppm.

2. A process according to claim 1 wherein said dithiocarbamate is incorporated into the water in a concentration between about 10 ppm and 500 ppm.

3. A process according to claim 1 wherein the sulfate-reducing bacteria are of the genus Desulfovibrio.

4. A process according to claim 1 wherein said dithiocarbamate is sodium N-benzyl, N-methyl-dithiocarbamate.

* * * * *